United States Patent
Allgeier

(10) Patent No.: US 7,132,562 B2
(45) Date of Patent: Nov. 7, 2006

(54) USE OF MODIFIERS IN A DINITRILE HYDROGENATION PROCESS

(75) Inventor: Alan Martin Allgeier, Wilmington, DE (US)

(73) Assignee: Invista North America S.A R.L., Wilmington, DE (US)

( * ) Notice: Subject to any disclaimer, the term of this patent is extended or adjusted under 35 U.S.C. 154(b) by 377 days.

(21) Appl. No.: 10/713,535

(22) Filed: Nov. 12, 2003

(65) Prior Publication Data

US 2005/0101797 A1    May 12, 2005

(51) Int. Cl.
*C07C 255/04*    (2006.01)
*C07C 209/04*    (2006.01)

(52) U.S. Cl. ...................... 558/459; 564/492
(58) Field of Classification Search ........... 558/459; 564/492
See application file for complete search history.

(56) References Cited

U.S. PATENT DOCUMENTS

| | | | |
|---|---|---|---|
| 3,758,584 A | 9/1973 | Bivens et al. | |
| 3,773,832 A | 11/1973 | Brake | |
| 5,151,543 A | 9/1992 | Ziemecki | |
| 6,110,856 A | 8/2000 | Flick et al. | |
| 6,258,745 B1 | 7/2001 | Ionkin et al. | |
| 6,376,714 B1 | 4/2002 | Allgeier et al. | |
| 6,566,297 B1 | 5/2003 | Ionkin | |

FOREIGN PATENT DOCUMENTS

| | | |
|---|---|---|
| GB | 728599 | 4/1955 |
| WO | WO 1999/047492 | 9/1999 |
| WO | WO 2002/096862 | 9/1999 |
| WO | WO 2003/006651 | 1/2003 |

*Primary Examiner*—Golam M. M. Shameem
*Assistant Examiner*—Ebenezer Sackey

(57) ABSTRACT

Catalytic process for hydrogenating a dinitrile to produce both aminocapronitrile and hexamethylenediamine in which the dinitrile is contacted with hydrogen in the presence of a catalyst and a modifier selected from the group consisting of quaternary ammonium hydroxides, cyanides, fluorides and thiocyanides; quaternary phosphonium hydroxide; carbon monoxide; and hydrogen cyanide.

5 Claims, No Drawings

USE OF MODIFIERS IN A DINITRILE HYDROGENATION PROCESS

FIELD OF THE INVENTION

The present invention concerns the hydrogenation of aliphatic dinitriles to produce diamines and/or aminonitriles, e.g. adiponitrile to produce hexamethylenediamine and/or 6-aminocapronitrile.

BACKGROUND OF THE INVENTION

Dinitriles are common feedstocks to the chemical, pharmaceutical, and agrochemical industries. Through hydrogenation they can be converted to diamines and/or aminonitriles, which are used in or as polymer intermediates, surfactants, chelating agents, and chemical synthesis intermediates. As a particular example, adiponitrile can be converted to 6-aminocapronitrile and/or hexamethylenediamine by hydrogenation. Hexamethylenediamine is an intermediate in the production of Nylon 6,6. 6-aminocapronitrile can be used as an intermediate in the production of Nylon 6.

Traditional methods of producing hexamethylenediamine include hydrogenation of adiponitrile over a reduced iron oxide or cobalt oxide catalyst at high pressures and temperatures. U.S. Pat. No. 6,110,856 describes the use of cobalt and iron based catalysts in a process for the hydrogenation of adiponitrile to a mixture of aminocapronitrile and hexamethylenediamine. The process does not produce aminocapronitrile with high selectivity, yielding 37% aminocapronitrile at 75% adiponitrile conversion. Low-pressure processes are known for the simultaneous production of aminocapronitrile and hexamethylenediamine. U.S. Pat. No. 5,151,543 describes the hydrogenation of dinitriles, including adiponitrile in the presence of a solvent. U.S. Pat. Nos. 6,258,745, 6,566,297, 6,376,714 and WO 99/47492 and WO 03/000651 A2 all describe the hydrogenation of dinitriles to aminonitriles in the presence of selectifying agents for low pressure reactions, i.e., 1 less than about 13.89 MPa (2000 psig).

For simultaneous production of aminonitrile and diamines, it would be advantageous to employ commercial equipment that is currently used for hexamethylenediamine production and that operates at high pressures, i.e. greater than 13.89 MPa (2000 psig). Additionally, it would be advantageous to operate these processes with increased selectivity to aminocapronitrile than is possible under operating conditions taught in the art.

SUMMARY OF THE INVENTION

The present invention is, a process of hydrogenating a dinitrile for the simultaneous production of aminocapronitrile and hexamethylenediamine, said process comprising treating the dinitrile with hydrogen in the presence of a catalyst and a modifier at a pressure of at least about 15.27 MPa (2200 psig), wherein said catalyst comprises an element selected from the group consisting of Fe, Ru, Co, and Ni and said modifier is at least one member selected from the group consisting of quaternary ammonium hydroxides, quaternary ammonium cyanides, quaternary ammonium fluorides, quaternary ammonium thiocyanates, quaternary phosphonium hydroxides, carbon monoxide, and hydrogen cyanide.

DETAILED DESCRIPTION OF THE INVENTION

In the present invention, an aliphatic or alicyclic dinitrile can be hydrogenated to a diamine or a mixture of a diamine and an aminonitrile using a catalyst at pressures greater than 15.27 MPa (2200 psig). For example, adiponitrile can be hydrogenated to hexamethylenediamine or a mixture of hexamethylenediamine and 6-aminocapronitrile. The process employs one or more modifiers to maintain or improve the selectivity of the process for the production of aminonitrile. These modifiers may react with the catalyst surface or may modify the reactivity of the dinitrile and/or aminonitrile. The modifiers may comprise quaternary ammonium hydroxide, cyanide, fluoride or thiocyanide salts, or quaternary phosphonium hydroxide salts or carbon monoxide or hydrogen cyanide. Notably, the modifiers of the present invention are not expected to build-up in the incinerator firebricks, nor are they expected to require disposal via deep-wells, when they or their decomposition products are removed from the crude product obtained from the said hydrogenation of dinitrile.

Suitable aliphatic or alicyclic dinitriles, for use herein, have the general formula $R(CN)_2$, wherein R is a saturated hydrocarbylene group. A saturated hydrocarbylene group contains carbon and hydrogen atoms in branched or straight chains or rings and does not contain a double or triple bond between any pair of carbon atoms. Preferred hydrocarbylene groups contain from 2 to 25, more preferably 2 to 15, and most preferably 2 to 10 carbon atoms per group. In other words, preferred dinitriles contain from 4 to 27, more preferably 4 to about 17, and most preferably 4 to 12, carbon atoms per dinitrile molecule. The preferred type of hydrocarbylene group is a linear alkylene group.

Examples of suitable dinitriles include, but are not limited to, adiponitrile; methylglutaronitrile; succinonitrile; glutaronitrile; alpha, omega-heptanedinitrile; alpha, omega-octanedinitrile, alpha, omega-decanedinitrile, alpha, omega-dodecanedinitrile; and combinations of two or more thereof. The preferred embodiment is adiponitrile (ADN).

The catalyst in the process is a hydrogenation catalyst suitable for hydrogenating a dinitrile to a diamine or a mixture of diamine and aminonitrile. Preferred are catalysts based on the elements iron, cobalt, nickel, or ruthenium and combinations thereof in which the said elements can exist as metals or their compounds. Most preferred is a catalyst comprising iron. The catalytic element may comprise about 1 to 99% of the total catalyst weight, preferably about 50 to 85 wt %. The catalyst may further comprise one or more promoters selected from the group consisting of aluminum, silicon, titanium, vanadium, magnesium, chromium, sodium, potassium and manganese. The promoters may be present in concentrations up to about 15% based on the total weight of the catalyst, preferably about 0.05 to 2 wt %.

While the degree of beneficial effects of this invention may vary with the structure of the dinitrile, the identity of the catalytic element, and the identity of the modifier, it is important to realize that even small improvements in selectivity can have large economic impact for large-scale industrial processes.

The catalytic element can also be supported on an inorganic support such as alumina, magnesium oxide, and combinations thereof. The element can be supported on an inorganic support by any means known to one skilled in the art such as, for example, impregnation, coprecipitation, ion exchange, and combinations of two or more thereof. If the catalytic element is supported on an inorganic support or is a component of an alloy or a solid solution, the catalytic element is generally present in the range of about 0.1 to about 60 wt % and preferably about 1 to about 50 weight percent, based on the total catalyst weight.

The catalyst can be present in any appropriate physical shape or form. It can be in fluidizable forms, extrudates, tablets, spheres, or combinations of two or more thereof. When employing the process using a fixed bed catalyst, the catalyst is in the form of granules having a particle size in the range of about 0.76 to 10.2 mm (0.03 to 0.40 inch). When employing the process using a slurry-phase catalyst, the catalyst is in finely divided form, preferably less than about 100 μm in size, most preferred range being about 20 to 75 μm.

The molar ratio of catalyst to dinitrile can be any ratio as long as the ratio can catalyze the selective hydrogenation of a dinitrile. The weight ratio of catalyst to dinitrile is generally in the range of from about 0.0001:1 to about 1:1, preferably about 0.001:1 to about 0.5:1.

The modifiers of the present invention can be selected from the group consisting of quaternary ammonium hydroxide, quaternary ammonium cyanide, quaternary ammonium fluoride, quaternary ammonium thiocyanides, quarternary phosphonium hydroxide, carbon monoxide and hydrogen cyanide. The term quaternary describes a nitrogen or phosphorous atom with four bonds to it and bearing a formal charge of +1. The ammonium ion ($NH_4^+$) and tetraalkylammonium ions are included within the definition of quaternary ammonium. More than one modifier can be used in the reaction. Examples of suitable modifiers are tetramethylammonium hydroxide, tetrabutylammonium cyanide, tetraethylammonium fluoride, tetrabutylammonium thiocyanide and tetrabutylphosphonium hydroxide. Preferred modifiers are quaternary ammonium hydroxide and quaternary ammonium cyanide. Examples of suitable tetraalkylammonium hydroxide compounds are tetramethylammonium hydroxide, tetraethylammoniu m hydroxide, tetrapropylammonium hydroxide and tetrabutylammonium hydroxide. Examples of suitable tetraalkylammonium cyanide compounds are tetramethylammonium cyanide, tetraethylammonium cyanide and tetrabutylammonium cyanide. It should be noted that various hydrated forms such as, for example, tetramethylammonium hydroxide pentahydrate, are included within the meaning of tetraalkylammonium hydroxide and tetraalkylphosphonium hydroxide.

The hydrogenation reaction can be conducted at a temperature of about 50 to 250° C. and preferably about 90 to 180° C. and at a pressure of about 15.27 to 55.26 MPa (2200 to 8000 psig) total pressure with hydrogen and preferably at about 20.78 to 34.58 MPa (3000 to 5000 psig). In a preferred mode of operation, the process is conducted continuously in a continuous stirred tank reactor (CSTR), a plug flow reactor (PFR), a slurry bubble column reactor (SBCR), or a trickle bed reactor. A continuous stirred tank reactor, also lcaown as a back-mixed reactor, is a vessel in which the reactants are added in a continuous fashion and a flow of product stream is continuously withdrawn from it. There is adequate mixing in the vessel provided by a mixing device, e.g. a mechanical agitator, so that the composition inside the reactor is uniform and is the same as that in the product stream withdrawn. A plug flow reactor is a tubular reactor in which the reactants are added in a continuous fashion in one end of the tubular reactor and the product is withdrawn in a continuous fashion from the other end of the tube. There is no back-mixing, i.e. the composition inside the reactor tube is not uniform. It is possible to incorporate backmixing in PFRs by recycling a part of the product flow back to the inlet of the reactor. It is also possible to achieve plug flow reactor behavior by using multiple CSTRs in series. A slurry bubble column reactor is a vessel, in which liquid reactants and gas are continuously fed to the bottom of the reartor, while product is continuously withdrawn from the top of the reactor. The gas is present in the reactor as bubbles, which rise and simultaneously provide mixing for a solid powdered catalyst (20 to 200 μm average particle sizes). The catalyst may be removed continuously with the product and added continuously by addition with the liquid feed. A trickle bed reactor is a tubular reactor in which the catalyst is fixed while the reactants are added at the top of the reactor and flow to the bottom where the product is continuously withdrawn. Gaseous reactants may flow cocurrently with the liquid or may flow countercurrendy from the bottom to the top of the reactor.

The preference for reactor is not meant to limit the invention, which can also be conducted in batch mode.

The process can be operated in the absence or presence of a solvent. In this invention, a solvent is defined as a substance that is added to a reaction mixture and that serves to solvate one or more reaction components, increases the volume of the reaction mixture, provides a medium for transferring (or removing) the heat of reaction, and is either not incorporated in the final product or does not alter the properties of the final product. While not comprehensive, a list of solvents includes ammonia; amines such as triethylamine; alcohols such as methanol, ethanol, propanol, and butanol; ethers such as tetrahydrofuran and dioxane; amides such diethylacetamide and N-methylpyrolidinone; and esters such as ethyl acetate and dimethyladipate. The preferred solvent is ammonia. The solvent can be present in the reaction mixture in about 20 to 90% by weight, preferably about 30 to 50%.

The modifier and dinitrile may be introduced to a reactor, which contains catalyst, separately or as a premixed solution with a diamine, an aminonitrile, water, a solvent or any combination thereof. The modifier can be added in a weight ratio to dinitrile from about 1:5000 to 1:30, preferably from about 1:2000 to 1:500.

The yields of diamine and/or aminonitrile, e.g. hexamethylenediamine and/or 6-aminocapronitrile, depend on operating conditions including temperature, pressure, hydrogen flow rate, amount and kind of catalyst, amount of modifier and space velocity and the like.

For the purpose of this invention, the term "space velocity" is defined as the unit weight of dinitrile fed into the reactor per hour, per unit weight of the catalyst. Typically, the dinitrile should be added to the reactor such that the space velocity of the dinitrile is within the range of about 0.5 to 20 $h^{-1}$. Most preferred space velocities may be readily determined by those skilled in the art using conventional techniques.

While not meant to limit the invention by any theory, it is possible that the modifier reacts with the element(s) of the catalyst forming a modifier/catalytic element complex. The resulting complex may contain the Group VIII element in its metallic state or perhaps in an oxidized state. The reaction of modifier with the catalytic element may be irreversible but more likely is a reversible equilibrium reaction. The interaction of the modifier with the catalyst may alter the reactivity of the catalyst, improve the selectivity for aminonitrile production, suppress secondary amine oligomer formation and, perhaps, increase the lifetime of the catalyst.

The catalyst and modifier can be separately introduced into a reactor to contact the dinitrile; however, the catalyst may be precontacted with the modifier. This may be done in water and/or a solvent such as, for example, an alcohol, ether, ester, ammonia, or combinations of two or more thereof.

The molar ratio of hydrogen to dinitrile is not critical as long as sufficient hydrogen is present to produce an aminonitrile and/or a diamine, e.g. 6-aminocapronitrile and/or hexamethylenediamine. Hydrogen is generally used in excess.

Diamine and/or aminonitrile, e.g. hexamethylenediamine and/or 6-aminocapronitrile, can be recovered from the reaction products by typical purification procedures such as recrystallization or preferably, distillation. The unreacted dinitrile can be recycled back to the hydrogenation reactor to obtain additional diamine and/or aminonitrile.

EXAMPLES

The hydrogenation of adiponitrile (ADN) may be described using a kinetic model in which ADN is first converted to aminocapronitrile (ACN) and the ACN is then converted to hexamethylenediamine (HMD), e.g., $$ADN \rightarrow ACN \rightarrow HMD$$

where each reaction step is a first order reaction, and the first step has a rate constant 2 $k_1$ and the second step has a rate constant $k_2$. In this model a $k_1/k_2=1$ value describes a non-selective catalyst and the maximum yield of ACN will be 50% in a well-mixed batch reaction. It is desirable to maximize the $k_1/k_2$ value.

Comparative Example 1

A 1-L stainless steel pressure vessel was charged with 216 g of adiponitrile and 20 g of a powdered, reduced iron catalyst. The vessel was sealed, purged with hydrogen and charged with 225 g ammonia. It was heated to 150° C. and pressurized to 4500 psig (31 MPa). As hydrogen was consumed, it was constantly replenished from a pressurized cylinder to maintain an operating pressure of 4500 psig (31 MN). After 70 min. the reaction was stopped, and a sample was analyzed via gas chromatography. The analysis showed that the reaction product comprised 12 wt % adiponitrile (ADN), 45 wt % 6-aminocapronitrile (ACN), and 36 wt % hexamethylenediamine. The $k_1/k_2$ value was 1.1.

Examples 2 to 4

The experiment of Example 1 was repeated except 0.2 g of a modifier chemical was added to the reaction mixture with the ADN. The results are presented in Table 1. TBACN=tetrabutylammonium cyanide, TEAF=tetraethylammonium cyanide, TMAHP=tetramethylammonium hydroxide pentahydrate.

| Example | Modifier | Time of Reaction (min) | Wt % ADN in reaction product | Wt % ACN in reaction product | Wt % HMD in reaction product | $k_1/k_2$ |
|---|---|---|---|---|---|---|
| 1 | None | 70 | 12 | 45 | 36 | 1.1 |
| 2 | TBACN | 315 | 21 | 57 | 17 | 1.8 |
| 3 | TEAF | 180 | 21 | 54 | 21 | 1.4 |
| 4 | TMAHP | 120 | 11 | 51 | 28 | 1.6 |

What is claimed:

1. A process of hydrogenating adiponitrile, said process comprising: contacting the adiponitrile with hydrogen in the presence of a catalyst and a modifier at a pressure of at least about 15.27 MPa (2200 psig), wherein said catalyst comprises an element selected from the group consisting of Fe, Ru, Co, and Ni and said modifier is at least one member selected from the group consisting of quaternary ammonium hydroxides, quaternary ammonium cyanides, quaternary ammonium fluorides, quaternary ammonium thiocyanates, quaternary phosphonium hydroxides, carbon monoxide, and hydrogen cyanide.

2. The process of claim 1 wherein the temperature is in the range of about 50° C. to 250° C.

3. The process of claim 1 wherein the pressure is in the range of about 20.7 to 34.5 MPa (3000 to 5000 psig).

4. The process of claim 1 wherein the catalyst comprises iron.

5. The process of claim 1 wherein the modifier comprises a quaternary ammonium cyanide or quaternary ammonium hydroxide salt.

* * * * *